United States Patent
Li

(10) Patent No.: US 12,383,697 B1
(45) Date of Patent: Aug. 12, 2025

(54) MOTION SICKNESS INTERVENTION METHOD BASED ON MINDFULNESS MEDITATION AND BRAIN-COMPUTER INTERFACE

(71) Applicant: South China Brain-computer Interface Technology Co., Ltd, Guangzhou (CN)

(72) Inventor: Yuanqing Li, Guangzhou (CN)

(73) Assignee: SOUTH CHINA BRAIN-COMPUTER INTERFACE TECHNOLOGY CO., Guangzhou (CN)

( * ) Notice: Subject to any disclaimer, the term of this patent is extended or adjusted under 35 U.S.C. 154(b) by 0 days.

(21) Appl. No.: 18/948,912

(22) Filed: Nov. 15, 2024

(30) Foreign Application Priority Data

Feb. 1, 2024 (CN) .......................... 202410143539.6

(51) Int. Cl.
  *A61M 21/02* (2006.01)
  *A61M 21/00* (2006.01)
  *G16H 20/70* (2018.01)

(52) U.S. Cl.
  CPC ............ *A61M 21/02* (2013.01); *G16H 20/70* (2018.01); *A61M 2021/0027* (2013.01); *A61M 2230/10* (2013.01)

(58) Field of Classification Search
  CPC .......... A61M 21/02; A61M 2021/0027; A61M 2230/10; G16H 20/70
  See application file for complete search history.

(56) References Cited

U.S. PATENT DOCUMENTS

| | | | |
|---|---|---|---|
| 2003/0144829 A1 | 7/2003 | Geatz et al. | |
| 2006/0161218 A1 | 7/2006 | Danilov | |
| 2023/0025019 A1* | 1/2023 | Youngblood | ........ G02B 27/017 |

FOREIGN PATENT DOCUMENTS

| | | |
|---|---|---|
| CN | 107684483 A | 2/2018 |
| CN | 108379713 A | 8/2018 |
| CN | 111048171 A | 4/2020 |
| CN | 111867459 A | 10/2020 |
| CN | 112568867 A | 3/2021 |
| CN | 112867528 A | 5/2021 |

(Continued)

OTHER PUBLICATIONS

International Search Report dated Sep. 12, 2024, for PCT Application No. PCT/CN2024/102862.

*Primary Examiner* — Carrie R Dorna
*Assistant Examiner* — Joshua Daryl D Lannu
(74) *Attorney, Agent, or Firm* — Karen A. LeCuyer; Yanjun Ma; DeWitt LLP

(57) ABSTRACT

Provided is a motion sickness intervention method based on mindfulness meditation and brain-computer interface. The method includes: collecting multi-channel/single-channel electroencephalographic (EEG) signals of the current user in real time; determining the motion sickness level from the multi-channel/single-channel EEG signals, where the motion sickness level includes a first level and a second level; and in response to the motion sickness level being the first level, performing a suspension operation; or in response to the motion sickness level being the second level, selecting a meditation feedback scenario and guiding the current user to meditate to alleviate motion sickness.

7 Claims, 1 Drawing Sheet

(56) References Cited

FOREIGN PATENT DOCUMENTS

| | | | |
|---|---|---|---|
| CN | 115105096 | A | 9/2022 |
| CN | 115151469 | A | 10/2022 |
| CN | 115738023 | A | 3/2023 |
| CN | 115768671 | A | 3/2023 |
| CN | 117653863 | A | 3/2024 |
| KR | 102508601 | * | 3/2023 |
| KR | 102508601 | B1 | 3/2023 |

* cited by examiner

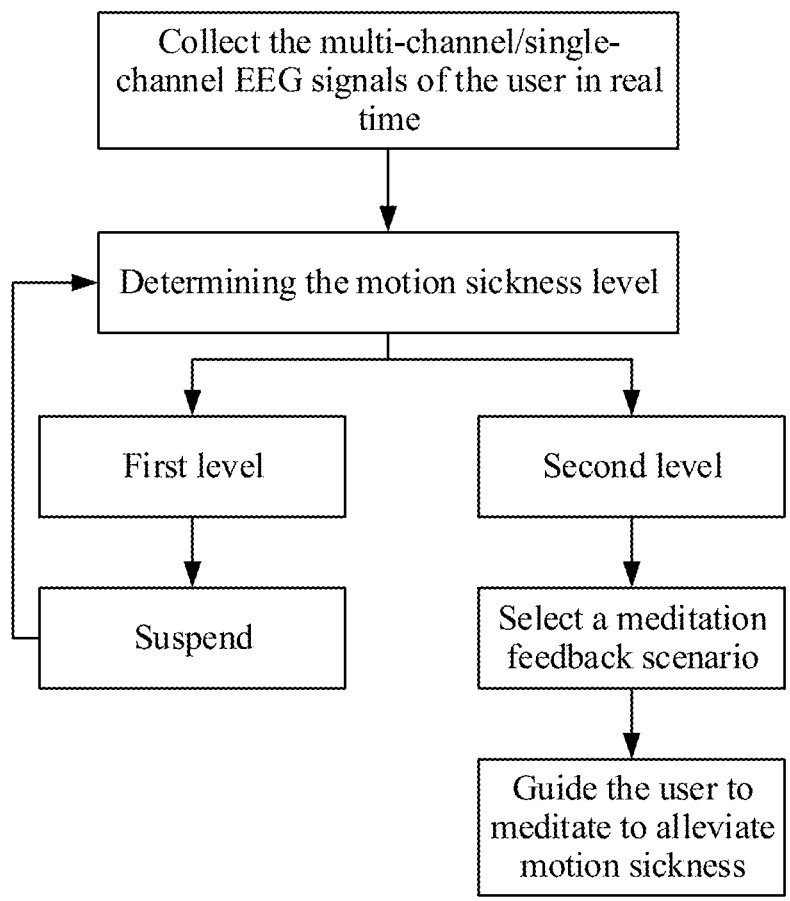

MOTION SICKNESS INTERVENTION METHOD BASED ON MINDFULNESS MEDITATION AND BRAIN-COMPUTER INTERFACE

CROSS-REFERENCE TO RELATED APPLICATION(S)

This application claims priority to Chinese Patent Application No. 202410143539.6 filed Feb. 1, 2024, the disclosure of which is incorporated herein by reference in its entirety.

TECHNICAL FIELD

The present disclosure relates to the field of brain-computer interface technologies, for example, a motion sickness intervention method based on the mindfulness meditation and the brain-computer interface.

BACKGROUND

When traveling by car, boat, or plane, some passengers may experience symptoms of motion sickness such as fainting, nausea, and loss of appetite, causing them noticeable discomfort. Currently, a common approach in addressing or preventing motion sickness is drug therapy. However, drug therapy may have side effects on passengers, and many passengers are unwilling to accept it, with its effectiveness varying from person to person. Passengers may also alleviate or prevent motion sickness by wearing special anti-motion-sickness glasses, with no noticeable effect for many passengers. In summary, currently no method can effectively relieve or prevent motion sickness without exerting side effects.

SUMMARY

The present disclosure provides a motion sickness intervention method based on the mindfulness meditation and the brain-computer interface to prevent or substantially alleviate motion sickness of a user in a vehicle.

The present disclosure provides the following solutions:

A motion sickness intervention method based on the mindfulness meditation and the brain-computer interface includes collecting the multi-channel/single-channel electroencephalographic (EEG) signals of the current user in real time; determining the motion sickness level from the multi-channel/single-channel EEG signals, where the motion sickness level includes a first level and a second level; and in response to the motion sickness level being the first level, performing a suspension operation; or in response to the motion sickness level being the second level, selecting a meditation feedback scenario and guiding the current user to meditate to alleviate motion sickness.

In a preferred solution of the present disclosure, before collecting the multi-channel/single-channel EEG signals of the current user in real time, the method also includes: collecting the multi-channel/single-channel EEG signals of historical users and using the multi-channel/single-channel EEG signals of the historical users as training data, where the historical users include users susceptible to motion sickness and users immune to motion sickness; building a training set that includes data pairs of user-reported motion sickness levels and the multi-channel/single-channel EEG signals of the historical users; and building a motion sickness assessment model based on the data pairs.

In a preferred solution of the present disclosure, determining the motion sickness level from the multi-channel/single-channel EEG signals includes: inputting the multi-channel/single-channel EEG signals of the current user to the motion sickness assessment model; outputting the motion sickness score of the current user; in response to the motion sickness score being within a first preset interval, determining that the motion sickness level is the first level, indicating that the current user experiences slight motion sickness symptom or no motion sickness symptom; in response to the motion sickness score being within a second preset interval, determining that the motion sickness level is the second level, indicating that the current user experiences noticeable motion sickness; and outputting the motion sickness level of the current user.

In a preferred solution of the present disclosure, outputting the motion sickness score of the current user includes: acquiring several preset motion sickness score intervals; and determining a target score interval corresponding to the motion sickness score according to the several motion sickness score intervals. The several motion sickness score intervals correspond to different motion sickness severity levels.

In a preferred solution of the present disclosure, inputting the multi-channel/single-channel EEG signals of the current user to the motion sickness assessment model includes: preprocessing the multi-channel/single-channel EEG signals of the current user to obtain to-be-tested EEG signal segments, where the preprocessing includes filtering processing; performing feature extraction on the to-be-tested EEG signal segments. The feature extraction includes extraction of at least one of a time domain feature, a frequency domain feature, or a time-frequency feature; and inputting the result of the feature extraction to the motion sickness assessment model.

In a preferred solution of the present disclosure, in response to the motion sickness level being the first level, performing the suspension operation includes: determining that the motion sickness level is the first level; collecting road condition information, where the road condition information includes a road condition with bumpiness and congestion, and a road condition with steadiness and smoothness; in response to the road condition being steadiness and smoothness, assessing the motion sickness level of the current user again according to a preset time interval; or in response to the road condition being bumpiness and congestion, selecting a meditation feedback scenario and guiding the current user to meditate. In response to the road condition being bumpiness and congestion, selecting the meditation feedback scenario and guiding the current user to meditate includes: collecting gyroscope signals; receiving traffic status information, where the traffic status information includes congestion status; and in response to the gyroscope signals satisfying a preset bumpiness condition and the traffic status information satisfying a preset condition, selecting the meditation feedback scenario and guiding the current user to meditate to prevent or alleviate motion sickness.

In a preferred solution of the present disclosure, in response to the motion sickness level being the second level, selecting the meditation feedback scenario and guiding the current user to meditate to alleviate the motion sickness includes: determining that the motion sickness level is the second level; voice-reminding the current user to start to meditate; selecting the meditation feedback scenario; calculating a meditation effect score based on the multi-channel/ single-channel EEG signals of the current user; and updating the meditation feedback scenario according to the meditation effect score.

The meditation feedback scenario includes at least one of visual feedback, auditory feedback, audiovisual feedback, olfactory feedback, tactile feedback, or electrical stimulation feedback.

Before calculating the meditation effect score, the method also includes: collecting the multi-channel/single-channel EEG signals of historical users in the relaxed state and the multi-channel/single-channel EEG signals of the historical users in the meditation state and using the multi-channel/single-channel EEG signals of the historical users in the relaxed state and the multi-channel/single-channel EEG signals of the historical users in the meditation state as training data; and building a meditation level assessment model based on the training data.

In a preferred solution of the present disclosure, calculating the meditation effect score based on the multi-channel/single-channel EEG signals of the current user includes: inputting the multi-channel/single-channel EEG signals of the current user to the meditation level assessment model; and outputting the meditation effect score of the current user.

In a preferred solution of the present disclosure, updating the meditation feedback scenario according to the meditation effect score includes: in response to the meditation effect score decreasing, reducing the expressive force of the meditation feedback scenario; or in response to the meditation effect score increasing, improving the expressive force of the meditation feedback scenario.

In a preferred solution of the present disclosure, the current user rides a vehicle that causes motion sickness. The vehicle that causes the motion sickness includes one of a car, a boat, or an aircraft.

Compared with the related art, the present disclosure has the following beneficial effects:

While riding a vehicle, the user performs mindfulness meditation based on a brain-computer interface, receives multisensory feedback, and adjusts the focus of attention in real time, thereby relaxing both mind and body and effectively preventing or alleviating motion sickness. Compared with existing visual compensation and drug intervention, the present disclosure has advantages such as having no side effect and having a noticeable intervention effect.

The present disclosure provides a motion sickness intervention method based on multi-channel/single-channel EEG signals and real-time road condition information. When the user is detected to experience noticeable motion sickness or the current road condition is bumpiness or congestion, the user is voice-reminded to start mindfulness meditation to timely alleviate or prevent motion sickness.

The present disclosure creatively proposes cross-user and cross-time motion sickness assessment model and meditation level assessment model. That is, the current user is not required to collect the electroencephalogram training data in advance; instead, the current user can directly use the models to assess the current state and output a motion sickness score and a meditation effect score.

The present disclosure can also collect the multi-channel/single-channel EEG signals of the current user in advance and use the signals to train or fine tune the motion sickness assessment model and meditation level assessment model.

For different levels of motion sickness, the present disclosure recommends to the user meditation scenarios of different feedback types including visual feedback, auditory feedback, audiovisual feedback, olfactory feedback, tactile feedback, and electrical stimulation feedback and also allows the user to autonomously select a meditation feedback scenario, thereby effectively improving the meditation effect of the user and facilitating mindfulness meditation.

The present disclosure has a wide scope of application and is not limited to a particular vehicle. The present disclosure can be applied to a car, a boat, an aircraft, or other scenarios where motion sickness is prone to occur.

BRIEF DESCRIPTION OF DRAWINGS

FIG. 1 is a flowchart of a motion sickness intervention method.

DETAILED DESCRIPTION

Solutions in embodiments of the present disclosure are described clearly and completely in conjunction with the drawings in the embodiments of the present disclosure. Apparently, the embodiments described are part, not all, of the embodiments of the present disclosure. Based on embodiments of the present disclosure, all other embodiments obtained by those of ordinary skill in the art without creative work are within the scope of the present disclosure.

Referring to FIG. 1, the motion sickness intervention method based on the mindfulness meditation and the brain-computer interface according to the present disclosure includes: collecting the multi-channel/single-channel electroencephalographic (EEG) signals of the current user in real time; determining the motion sickness level from the multi-channel/single-channel EEG signals, where the motion sickness level includes a first level and a second level; and if the motion sickness level is the first level, performing a suspension operation; or if the motion sickness level is the second level, selecting a meditation feedback scenario and guiding the current user to meditate to alleviate motion sickness.

The motion sickness level may be classified into a first level and a second level. The first level refers to no motion sickness or acceptable slight motion sickness. The second level refers to (intolerable) severe motion sickness.

The suspension operation is an operation of continuing determining the motion sickness level from the multi-channel/single-channel EEG signals.

The meditation feedback scenario is selected from preset meditation feedback scenarios. When the user use the motion sickness intervention method for the first time, the user can select an initial default meditation scenario from the meditation feedback scenarios. The user can also customize a feedback scenario according to the usage habit of the user.

By determining the motion sickness level and performing continuous detection operation or guided meditation operation, multisensory feedback is received, and the focus of attention is adjusted in real time, thereby relaxing both mind and body and effectively preventing or alleviating motion sickness. Compared with existing visual compensation and drug intervention, the present disclosure has advantages such as having no side effect and having a noticeable intervention effect.

In this embodiment, preferably, before collecting the multi-channel/single-channel EEG signals of the current user in real time, the method also includes: collecting the multi-channel/single-channel EEG signals of historical users and using the multi-channel/single-channel EEG signals of the historical users as training data, where the historical users include users susceptible to motion sickness and users immune to motion sickness; building a training set that includes data pairs of user-reported motion sickness levels and the multi-channel/single-channel EEG signals of the historical users; and building a motion sickness assessment model based on the data pairs.

The motion sickness assessment model is built as follows:

(1) Signal Acquisition: Acquisition of multi-channel/single-channel electroencephalographic (EEG) signals from participants, encompassing both users susceptible and immune to motion sickness (e.g., 100 instances per category), during their use of transportation vehicles. The equipment utilized for signal collection includes the Neuroscan and the multi-channel/single-channel headbands provided by South China Brain-computer Interface Technology Co., Ltd.

(2) Signal processing:

2.1. The collected EEG signals are preprocessed: The collected EEG signals are divided into equally long (for example, 5 s) EEG signal segments, where each EEG signal segment constitutes a sample.

2.2. Bandpass filtering is performed on each sample by using a filter, and the filter may adopt a Chebyshev filter or a Butterworth bandpass filter.

2.3. Feature extraction is performed on the preprocessed samples. The feature extraction includes extraction of at least one of a time domain feature, a frequency domain feature, or a time-frequency feature.

(3) Data tagging: Each EEG signal segment is tagged as motion sickness or no noticeable motion sickness according to user-reported motion sickness symptoms.

(4) Model training: A machine learning model such as a support vector model or a random forests model is built, or a deep network model such as a convolutional neural network model or a recurrent neural network model is built; and the model is trained by using the feature extraction result and the corresponding motion sickness tag, and a motion sickness assessment model having fixed parameters is output. This motion sickness assessment model can be used for intra-subject, cross-subject, and cross-temporal motion sickness assessment.

In this embodiment, preferably, determining the motion sickness level from the multi-channel/single-channel EEG signals includes: inputting the multi-channel/single-channel EEG signals of the current user to the motion sickness assessment model; outputting the motion sickness score of the current user; in response to the motion sickness score being within a first preset interval, determining that the motion sickness level is the first level, indicating that the current user experiences slight motion sickness symptom or no motion sickness symptom; in response to the motion sickness score being within a second preset interval, determining that the motion sickness level is the second level, indicating that the current user experiences noticeable motion sickness; and outputting the motion sickness level of the current user.

Motion sickness scores may be divided into a first level and a second level. For example, motion sickness scores range from 0 to 10. In this case, it is feasible to set the first preset interval from 0 (inclusive) to 3 (exclusive) and the second preset interval from 3 (inclusive) to 10 (inclusive). The motion sickness level of the current user is determined according to the motion sickness score of the current user.

The motion assessment model can be used to assess the current state of the user and output the motion sickness score and the meditation effect score without collecting the EEG training data of the current user in advance. The present disclosure may also collect the multi-channel/single-channel EEG signals of the current user in advance and use the signals to train or fine tune the motion sickness assessment model and the meditation level assessment model.

In this embodiment, preferably, outputting the motion sickness score of the current user includes: acquiring several preset motion sickness score intervals; and determining a target score interval corresponding to the motion sickness score according to the several motion sickness score intervals. The several motion sickness score intervals correspond to different motion sickness severity levels.

Motion sickness scores may not only be divided into a first level and a second level, but can also be divided into multiple levels. For example, motion sickness scores range from 0 to 10. In this case, it is feasible to set one preset interval from 0 (inclusive) to 3 (exclusive), indicating that the current user experiences no motion sickness symptom; set one preset interval to 3 (inclusive) to 6 (exclusive), indicating that the current user experiences slight motion sickness symptoms; and set one preset interval to 6 (inclusive) to 10 (inclusive), indicating that the current user experiences noticeable motion sickness symptoms.

In this embodiment, preferably, inputting the multi-channel/single-channel EEG signals of the current user to the motion sickness assessment model includes: preprocessing the multi-channel/single-channel EEG signals of the current user to obtain to-be-tested EEG signal segments, where the preprocessing includes filtering processing; performing feature extraction on the to-be-tested EEG signal segments, where the feature extraction includes extraction of at least one of a time domain feature, a frequency domain feature, or a time-frequency feature; and inputting the result of the feature extraction to the motion sickness assessment model.

In this embodiment, preferably, if the motion sickness level is the first level, performing the suspension operation includes: determining that the motion sickness level is the first level; collecting road condition information, where the road condition information includes a road condition with bumpiness and congestion, and a road condition with steadiness and smoothness; if the road condition is steadiness and smoothness, assessing the motion sickness level of the current user again according to a preset time interval; or if the road condition is bumpiness or congestion, selecting a meditation feedback scenario and guiding the current user to meditate. If the road condition is bumpiness and congestion, selecting the meditation feedback scenario and guiding the current user to meditate includes: collecting gyroscope signals; receiving traffic status information, where the traffic status information includes congestion status; and if the gyroscope signals satisfy a preset bumpiness condition and the traffic status information satisfies a preset condition, selecting the meditation feedback scenario and guiding the current user to meditate to prevent or alleviate motion sickness.

When the motion sickness level is the first level, road condition information is collected. Generally, signals collected from a gyroscope and traffic status information called from third-party software are used as the road condition information. The road condition information includes a road condition with bumpiness and congestion, and a road condition with steadiness and smoothness. The road condition with bumpiness and congestion refers to a condition such as a traffic jam, road construction, an accident, or continuous turns. The road condition with steadiness and smoothness refers to absence of traffic abnormalities, allowing vehicles to travel smoothly. If the road condition is steadiness and smoothness, the motion sickness level of the current user is assessed again according to a preset time interval. If the road condition is bumpiness and congestion, a meditation feedback scenario is selected, and the current user is guided to meditate, thereby timely alleviating or preventing motion sickness.

In this embodiment, preferably, if the motion sickness level is the second level, selecting the meditation feedback scenario and guiding the current user to meditate to alleviate the motion sickness includes: determining that the motion sickness level is the second level; voice-reminding the current user to start to meditate; selecting the meditation feedback scenario; calculating a meditation effect score based on the multi-channel/single-channel EEG signals of the current user; and updating the meditation feedback scenario according to the meditation effect score.

The meditation feedback scenario includes at least one of visual feedback, auditory feedback, audiovisual feedback, olfactory feedback, tactile feedback, or electrical stimulation feedback.

Before calculating the meditation effect score, the method also includes: collecting the multi-channel/single-channel EEG signals of historical users in the relaxed state and the multi-channel/single-channel EEG signals of the historical users in the meditation state and using the multi-channel/single-channel EEG signals of the historical users in the relaxed state and the multi-channel/single-channel EEG signals of the historical users in the meditation state as training data; and building a meditation level assessment model based on the training data.

The meditation level assessment model is built as follows:
(1) Signal collection: The multi-channel/single-channel EEG signals of multiple users (for example, 100 users) in the relaxed state (or in a calm state) and the multi-channel/single-channel EEG signals of these users in the meditation state are collected by using a collection device, and the collection device includes Neuroscan or the multi-channel/single-channel headbands provided by South China Brain-computer Interface Technology Co., Ltd.
(2) Signal processing:
2.1. The collected EEG signals are preprocessed: The collected EEG signals are divided into equally long (for example, 10 s) EEG signal segments, where each EEG signal segment constitutes a sample.
2.2. Bandpass filtering is performed on each sample by using a filter, and the filter may adopt a Chebyshev filter or a Butterworth bandpass filter.
2.3. Feature extraction is performed on the preprocessed samples. The feature extraction includes extraction of at least one of a time domain feature, a frequency domain feature, or a time-frequency feature.
(3) Model design: A machine learning model such as a support vector model or a random forests model is built, or a deep network model such as a convolutional neural network model or a recurrent neural network model is built. This model can be used for intra-subject, cross-subject, and cross-temporal meditation level assessment.
(4) Model output: The model built in (3) is trained by using the feature extraction result and the corresponding relaxed state or meditation state tag, and after the training is completed, the meditation level assessment model having fixed parameters is output.

In this embodiment, preferably, calculating the meditation effect score based on the multi-channel/single-channel EEG signals of the current user includes: inputting the multi-channel/single-channel EEG signals of the current user to the meditation level assessment model; and outputting the meditation effect score of the current user.

In this embodiment, preferably, updating the meditation feedback scenario according to the meditation effect score includes: in response to the meditation effect score decreasing, reducing the expressive force of the meditation feedback scenario; or in response to the meditation effect score increasing, improving the expressive force of the meditation feedback scenario.

The meditation feedback scenario is a scenario where the user is guided to meditate and make a self-adjustment according to the user feedback (represented as the meditation effect score). The meditation feedback scenario includes but is not limited to a visual scenario, an auditory scenario, a tactile scenario, and an olfactory scenario. In a visual scenario, expressiveness typically refers to the clarity of an image. In an auditory scenario, expressiveness typically refers to the clarity of sound and the volume and strength of background noise. In a tactile scenario, expressiveness typically refers to the vibration magnitude of a wearable device or the intensity of electrical stimulation. In an olfactory scenario, expressiveness typically refers to the concentration and pleasantness of an odor.

That is, for different levels of motion sickness, the present disclosure recommends to the user meditation scenarios of different feedback types including visual feedback, auditory feedback, audiovisual feedback, olfactory feedback, tactile feedback, and electrical stimulation feedback and also allows the user to autonomously select a meditation feedback scenario, thereby effectively improving the meditation effect of the user and reducing the threshold for entering the meditation state.

In this embodiment, preferably, the current user rides a vehicle that causes motion sickness. The vehicle that causes the motion sickness includes one of a car, a boat, or an aircraft.

In a feasible implementation scenario, the motion sickness intervention method based on the mindfulness meditation and the brain-computer interface is as follows:
(1) The user puts on an EEG signal collection device and transmits EEG signals to a computing device such as a vehicle-mounted computer, a notebook computer, a tablet computer, or a smartphone in real time via Bluetooth or wired communication.
(2) The computing device processes the EEG signals, the processing of the EEG signals includes: segmentation, baseline removal, filtering, and feature extraction.
(3) The processed EEG signals are input to the motion sickness assessment model, and the motion sickness assessment score is output.
(4) The motion sickness status of the current user is determined according to the interval where the motion sickness score is located. For example, the scores range from 1 to 100.
4.1. If the motion sickness score is within [1, a] (for example, a is 20), the user experiences no motion sickness symptom and corresponds to the first motion sickness level. If the motion sickness score is within (a, 100] (for example, a is 20), the user experiences noticeable motion sickness symptoms and corresponds to the second motion sickness level.
4.2. It is also feasible to subdivide the motion sickness scores and then output the assessment result. For example, the motion sickness scores ranging from 1 to 20 indicates no motion sickness symptom, the motion sickness scores ranging from 21 to 70 indicates slight motion sickness symptom, and the motion sickness scores ranging from 71 to 100 indicates severe motion sickness symptom.

(5) If the user is at the second motion sickness level, the user is voice-reminded to start mindfulness meditation. At this time, a mindfulness meditation system is automatically started and automatically recommends a feedback scenario for mindfulness meditation to the user; or the user may select a preferred scenario for mindfulness meditation to alleviate motion sickness.

5.1. The meditation feedback scenario is displayed by the screen and speaker of a vehicle-mounted computer, a notebook computer, a tablet computer, or a smartphone, or by an electrical stimulation device.

5.2. After entering the meditation feedback scenario, the computing device inputs the preprocessed EEG signals to the meditation level assessment model, and the meditation effect score is output.

5.3. Based on the meditation effect score, the expressiveness of the meditation feedback scenario is controlled. The controlling of the expressiveness of the meditation feedback scenario includes variations in visual scenario clarity and viewing angle, variations in volume, pitch, and sound type in the auditory scenario, variations in tactile intensity, or variations in electrical stimulation intensity. In an embodiment, the user's meditation level is assessed at regular intervals (for example, every 2 s). When the meditation effect score at this moment is higher than that at the previous moment, indicating an improvement in the meditation depth/effect, the 3D/2D visual scenario becomes clearer and more beautiful, and the sound becomes louder. When the meditation effect score at this moment is lower than that at the previous moment, indicating a decrease in the meditation depth/effect, the 3D/2D scenario becomes vague and not beautiful, and the sound becomes lower.

5.4. Visual feedback scenarios may include animations of the sky, clouds, campfires, ocean waves, and forests. Auditory feedback scenarios may include pink noise, sounds of raindrops, flowing water, crackling flames, and music. Audiovisual feedback scenarios may include both visual feedback and auditory feedback. Olfactory feedback may include aromatherapy. Tactile feedback may include vibrations of portable devices and seat massages. Electrical stimulation feedback may include direct current stimulation. All of these sensory feedback scenarios are accompanied by meditation guidance to guide user training.

(6) If the user experiences no motion sickness symptom, gyroscope data is collected, traffic status information (called from third-party map software) is received, and the data is transmitted to the current computing device in a Bluetooth or wireless manner.

6.1. If the road condition is bumpiness and congestion, such as an excessive change of the gyroscope angular velocity or a traffic congestion fed back by the map software, a mindfulness meditation system is automatically started and automatically recommends a feedback scenario for mindfulness meditation to the user; or the user may select a preferred scenario for mindfulness meditation to alleviate motion sickness.

6.2. If the road condition is steadiness and smoothness, the user is not reminded to meditate.

Although embodiments of the present disclosure are illustrated and described earlier, it is to be understood by those skilled in the art that various modifications, alterations, substitutions, and variations may be made to these embodiments without departing from the principles and spirit of the present disclosure. The scope of the present disclosure is defined by the appended claims and their equivalents.

What is claimed is:

1. A motion sickness intervention method based on mindfulness meditation and a brain-computer interface, comprising:
   collecting multi-channel/single-channel electroencephalographic (EEG) signals of a current user in real time;
   determining a motion sickness level from the multi-channel/single-channel EEG signals, wherein the motion sickness level comprises a first level and a second level; and
   in response to the motion sickness level being the first level, performing a suspension operation; or
   in response to the motion sickness level being the second level, selecting a meditation feedback scenario and guiding the current user to meditate to alleviate motion sickness:
   before the collecting the multi-channel/single-channel EEG signals of the current user in real time, the method further comprising:
   collecting multi-channel/single-channel EEG signals of historical users and using the multi-channel/single-channel EEG signals of the historical users as training data, wherein the historical users comprise users susceptible to motion sickness and users immune to the motion sickness;
   building a training set, wherein the training set comprises data pairs of user-reported motion sickness levels and the multi-channel/single-channel EEG signals of the historical users; and
   building a motion sickness assessment model based on the data pairs;
   wherein the determining the motion sickness level from the multi-channel/single-channel EEG signals comprises:
   inputting the multi-channel/single-channel EEG signals of the current user to the motion sickness assessment model;
   determining and outputting a motion sickness score of the current user according to the multi-channel/single-channel EEG signals of the current user and the motion sickness assessment model;
   in response to the motion sickness score being within a first preset interval, determining that the motion sickness level is the first level, indicating that the current user experiences no or slight motion sickness symptoms;
   in response to the motion sickness score being within a second preset interval, determining that the motion sickness level is the second level, indicating that the current user experiences noticeable motion sickness symptoms; and
   outputting the motion sickness level of the current user;
   wherein in response to the motion sickness level being the first level, the performing the suspension operation comprises:
   determining that the motion sickness level is the first level;
   collecting road condition information, wherein the road condition information comprises a road condition with bumpiness and congestion, and a road condition with steadiness and smoothness;
   in response to the road condition being the steadiness and the smoothness, assessing the motion sickness level of the current user again according to a preset time interval; or in response to the road condition being the bumpiness and the congestion, selecting the meditation feedback scenario and guiding the current user to meditate, wherein in response to the road condition being the bumpiness and the congestion, selecting the meditation feedback scenario and guiding the current user to meditate comprises:

collecting gyroscope signals;

receiving traffic status information, wherein the traffic status information comprises congestion status; and in response to the gyroscope signals satisfying a preset bumpiness condition and the traffic status information satisfying a preset condition, selecting the meditation feedback scenario and guiding the current user to meditate to prevent or alleviate motion sickness;

wherein in response to the motion sickness level being the second level, the selecting the meditation feedback scenario and guiding the current user to meditate to alleviate the motion sickness comprises:

determining that the motion sickness level is the second level;

voice-reminding the current user to start to meditate;

selecting the meditation feedback scenario;

calculating a meditation effect score based on the multi-channel/single-channel EEG signals of the current user; and updating the meditation feedback scenario according to the meditation effect score, wherein the meditation feedback scenario comprises at least one of visual feedback, auditory feedback, audio-visual feedback, olfactory feedback, tactile feedback, or electrical stimulation feedback; and wherein before calculating the meditation effect score, the method further comprises:

collecting multi-channel/single-channel EEG signals of the historical users in a relaxed state and multi-channel/single-channel EEG signals of the historical users in a meditation state and using the multi-channel/single-channel EEG signals of the historical users in the relaxed state and the multi-channel/single-channel EEG signals of the historical users in the meditation state as training data; and building a meditation level assessment model based on the training data;

wherein the motion sickness is caused by the current user riding a vehicle.

2. The motion sickness intervention method based on the mindfulness meditation and the brain-computer interface according to claim 1, wherein outputting the motion sickness score of the current user comprises:

acquiring a plurality of preset motion sickness score intervals; and determining a target score interval corresponding to the motion sickness score according to the plurality of several motion sickness score intervals, wherein the plurality of preset motion sickness score intervals correspond to different motion sickness severity levels.

3. The motion sickness intervention method based on the mindfulness meditation and the brain-computer interface according to claim 1, wherein the inputting the multi-channel/single-channel EEG signals of the current user to the motion sickness assessment model comprises:

preprocessing the multi-channel/single-channel EEG signals of the current user to obtain to-be-tested EEG signal segments, wherein the preprocessing comprises filtering processing;

performing feature extraction on the to-be-tested EEG signal segments, wherein the feature extraction comprises extraction of at least one of a time domain feature, a frequency domain feature, or a time-frequency feature; and inputting a result of the feature extraction to the motion sickness assessment model.

4. The motion sickness intervention method based on the mindfulness meditation and the brain-computer interface according to claim 1, wherein the calculating the meditation effect score based on the multi-channel/single-channel EEG signals of the current user comprises:

inputting the multi-channel/single-channel EEG signals of the current user to the meditation level assessment model; and outputting the meditation effect score of the current user.

5. The motion sickness intervention method based on the mindfulness meditation and the brain-computer interface according to claim 1, wherein updating the meditation feedback scenario according to the meditation effect score comprises:

in response to the meditation effect score decreasing, reducing an expressive force of the meditation feedback scenario; or in response to the meditation effect score increasing, improving the expressive force of the meditation feedback scenario.

6. The motion sickness intervention method based on the mindfulness meditation and the brain-computer interface according to claim 1, wherein the vehicle that causes the motion sickness comprises one of a car, a boat, or an aircraft.

7. The motion sickness intervention method based on the mindfulness meditation and the brain-computer interface according to claim 1, wherein determining and outputting the motion sickness score of the current user according to the multi-channel/single-channel EEG signals of the current user and the motion sickness assessment model comprises:

calculating and outputting the motion sickness score of the current user according to the multi-channel/single-channel EEG signals of the current user, a pre-trained feature extraction result of the multi-channel/single-channel EEG signals of the historical users and a motion sickness tag corresponding to the pre-trained feature extraction result of the multi-channel/single-channel EEG signals of the historical users in the motion sickness assessment model, wherein the motion sickness score is a probability value of matching a feature extraction result of the multi-channel/single-channel EEG signals of the current user with the motion sickness tag corresponding to the pre-trained feature extraction result of the multi-channel/single-channel EEG signals of the historical users in the motion sickness assessment model.

* * * * *